United States Patent [19]

van Veen et al.

[11] Patent Number: 5,105,942
[45] Date of Patent: Apr. 21, 1992

[54] PACKAGING

[75] Inventors: Jimmy E. van Veen; Arjan Kremer, both of Roden, Netherlands

[73] Assignee: Cordis Corporation, Miami Lakes, Fla.

[21] Appl. No.: 597,052

[22] Filed: Oct. 15, 1990

[30] Foreign Application Priority Data

Oct. 16, 1989 [NL] Netherlands ............ 8902563
Jul. 4, 1990 [NL] Netherlands ............ 9001525

[51] Int. Cl.$^5$ ............................................. B65D 83/10
[52] U.S. Cl. ................................. 206/364; 206/363; 206/438; 206/439; 206/461; 206/471
[58] Field of Search ............ 206/363, 364, 438, 439, 206/461, 471, 484.1, 486, 303, 306; 220/670, 672, 675

[56] References Cited

U.S. PATENT DOCUMENTS

| | | | |
|---|---|---|---|
| 3,035,691 | 5/1962 | Rasmussen et al. | 206/364 |
| 3,104,172 | 9/1963 | Wizelman . | |
| 3,123,210 | 3/1964 | Hermanson et al. | 206/363 |
| 3,353,664 | 11/1967 | Armentrout et al. | 206/461 |
| 3,472,418 | 10/1969 | Ullman | 220/672 |
| 3,495,736 | 2/1970 | Ragettli | 220/670 |
| 3,595,465 | 7/1971 | Vaillancourt | 220/439 |
| 3,612,038 | 10/1971 | Halligan | 206/364 |
| 3,633,758 | 1/1972 | Morse | 206/364 |
| 3,750,875 | 8/1973 | Juster | 206/364 |
| 3,809,221 | 5/1974 | Compere | 206/461 |
| 3,839,841 | 10/1974 | Amplatz . | |
| 3,910,410 | 10/1975 | Shaw | 206/363 |
| 4,019,633 | 4/1977 | Roth | 206/364 |
| 4,135,509 | 1/1979 | Shannon | 206/364 |
| 4,248,236 | 2/1981 | Linder | 206/364 |
| 4,256,225 | 3/1981 | Jackson | 206/303 |
| 4,262,800 | 4/1981 | Nethercutt | 206/364 |
| 4,269,310 | 5/1981 | Uson | 206/364 |
| 4,324,331 | 4/1982 | Ignasiak | 206/461 |
| 4,379,506 | 4/1983 | Davidson | 206/438 |
| 4,923,061 | 5/1990 | Trombley, III | 206/364 |

FOREIGN PATENT DOCUMENTS

WO89/04685 6/1989 PCT Int'l Appl. .

Primary Examiner—David T. Fidei
Attorney, Agent, or Firm—Gerstman & Ellis, Ltd.

[57] ABSTRACT

Packaging such as a blister pack is provided for at least one element such as a catheter having a thin, elongated portion. The packaging comprises at least two elongated, flexible sheets adhered to each other, which form between them a space for receiving the element such as the catheter. By this invention, the space is formed by a pressed-out or outwardly projecting portion generally corresponding to the shape of the element in at least one of the sheets. The sheet, in the part of the pressed-out portion corresponds with the thin, elongated portion of the element, has an at least partly corrugated profile. Also, the catheter packaged herein may have a distal end curved in a predetermined shape, in which the part of the pressed-out portion corresponding with the curved distal catheter end is locked within the pressed-out portion, to prevent distortion of the catheter tip out of the particular shape. Also, preferably, one or both of the flexible sheets define a layer of polyethylene on their inner surface to protect the catheter or other product from damage upon removal thereof.

19 Claims, 4 Drawing Sheets

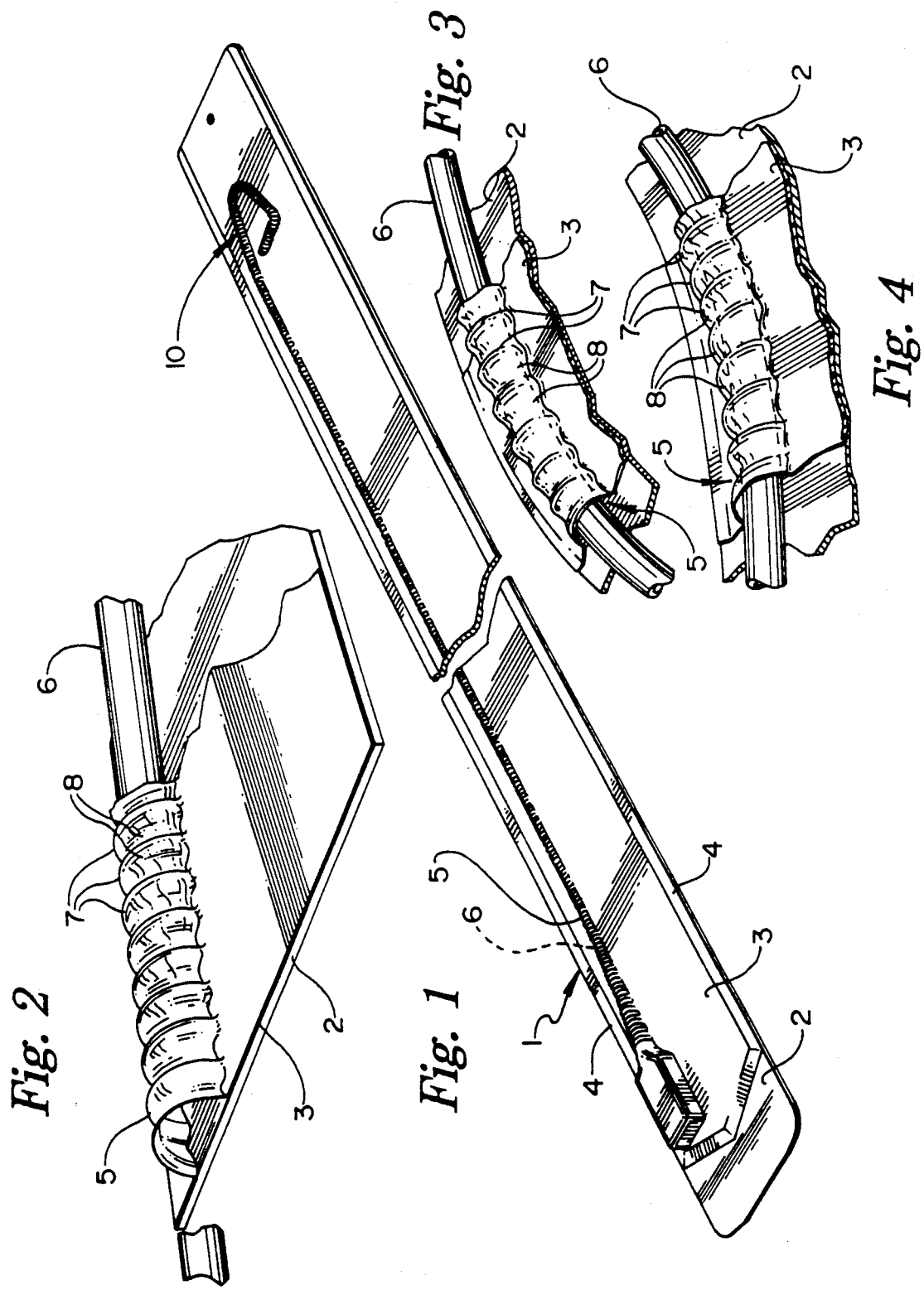

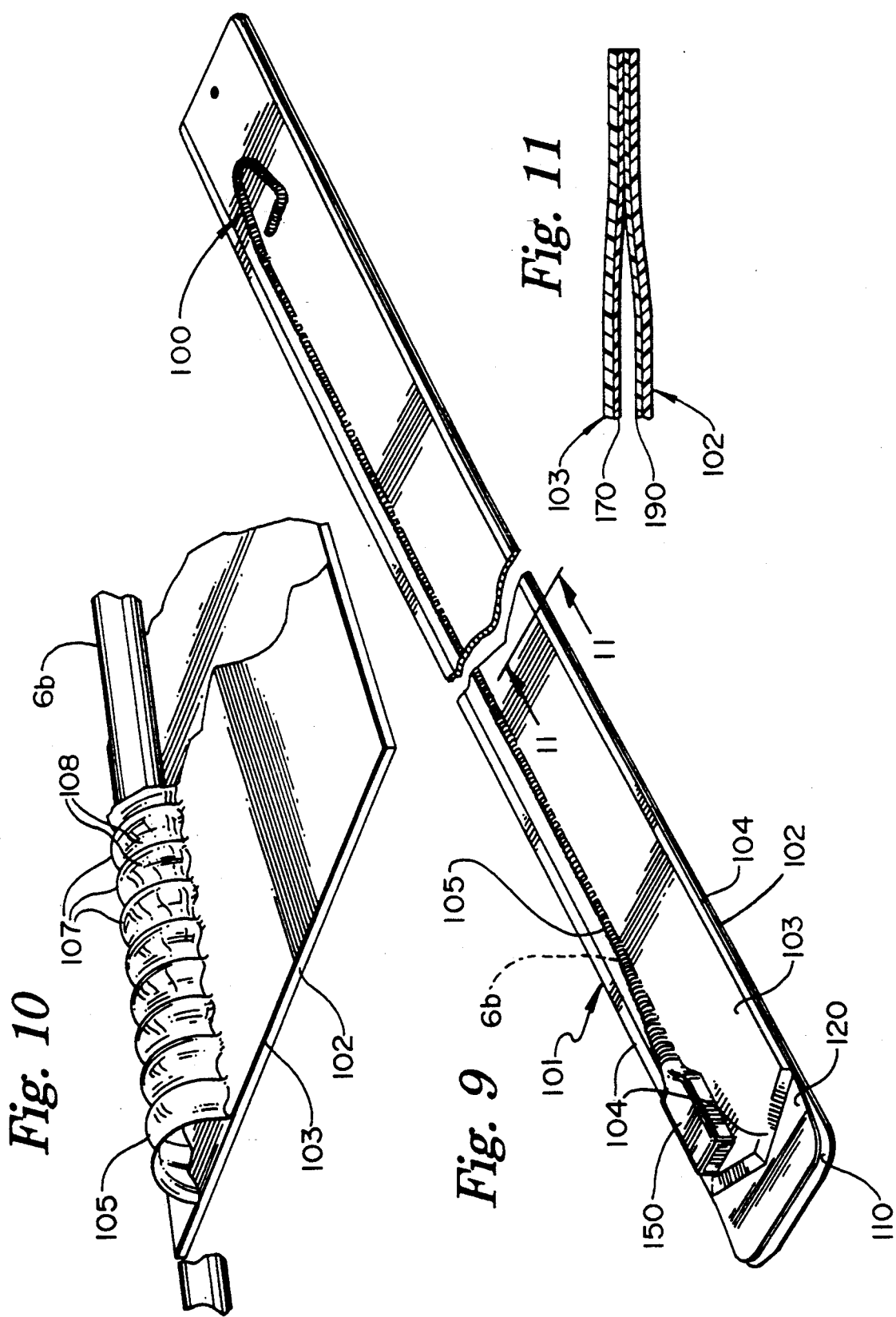

PACKAGING

BACKGROUND OF THE INVENTION

The invention relates to a packaging for an element with a thin, elongated portion comprising at least two elongated, flexible sheets peripherally adhered to one another and forming between them a space for receiving the element. The two elongated, flexible sheets can form an envelope wherein the element is arranged.

With catheters it is for example known to package them by attaching them first to a plastic or cardboard sheet or tray, and to insert them with the sheet or tray into an envelope. Attachment can take place through punched lips in the cardboard being bent outwardly and the catheter being clamped thereunder. The packaging of a catheter in this way is laborious and time-consuming.

The invention now has for a first object a packaging of the type described above, wherein an element with a thin, elongated part can be packaged in an economical manner.

As another aspect of this invention, it is conventional to open packaging of the type described above by pulling the two elongated, flexible sheets of the package free of one another at one end thereof, thus rupturing the peripheral seal line. Then, when the proximal end of the catheter is exposed, the user grasps the hub or connecting member thereof and pulls the catheter out of the package.

It has been found that catheters packed and opened in this manner can exhibit damage after removal. Particularly, one or more small, flat areas are formed on the distal, curved tip of the catheter. While these flat areas are scarcely visible to the naked eye, they are of a nature that can make rejection of the catheter necessary. For example, if such defects resulted during manufacture of the catheter, the catheter might be rejected as of poor quality.

Since the original, packed catheters are undamaged, but they display such damage after removal from the packaging, it has been concluded that the damage to the catheters occurs between the moment of packaging and the moment following their removal from the packaging.

Thus, a second object of this invention is to provide a blister packaging of the type specified which better protects its contents such as catheters from damage.

DESCRIPTION OF THE INVENTION

With the packaging according to the invention the first object described above is achieved. A space is formed by a pressed-out portion in one of the package sheets, corresponding with the thin elongated portion of the element to be packaged, and the pressed-out portion has a corrugated profile. The element for packaging, such as a catheter, can thereby be better arranged in the pressed-out portion and fixed therein in a reliable manner without having to be fixed beforehand onto an extra sheet or tray.

The packaging can be embodied thereby as a per se known "blister pack". As a result of the corrugated profiling of the part of the pressed-out portion corresponding with the thin, elongated portion of the element, that package portion is highly flexible without creating risk of the material of the sheet buckling or tearing at the location of the pressed-out portion. With prior art packaging for catheters, such buckling could render the catheter unusable, and package tearing could cause the loss of the sterility thereof.

Blister packs are of course per se known. By this invention it has, however, become possible to arrange in a suitable manner in a blister pack a thin, elongated element or an element comprising a thin, elongated portion, which was less easily done in the prior art.

An attendant advantage of the packaging according to the invention, after use it can be easily crumpled up so that the packaging can be thrown away and disposed of without problems.

The invention also relates to and provides an assembly of a packaging as described above and a catheter packaged therein. When the packaged catheter has an outer or distal end curved in a particular, desired shape, as is usual with catheters for angiographic purposes, the packaging is preferably arranged so that the part of the pressed-out portion corresponding with the curved outer end of the catheter is formed of a shape to lock the curved outer end of the catheter in its desired shape.

It is usual to curve the outer ends of catheters into the desired shape when they are heated, whereupon the curved form is fixed therein as a result of cooling. See for example PCT International Publication No. WO89/04685. After packaging of the catheter, sterilization is generally required. In a predetermined phase of the sterilization process, the assembly of packaging and catheter may be heated. In the case of a packaging according to the state of the art the danger exists that the curved catheter outer end curves out slightly because of the raised temperature, and thereby no longer has the desired form. By holding the catheter tip in the shaped, pressed-out portion of this invention, the curved outer catheter end also remains accurately fixed in the correct, particular form during the heating phase of the sterilization process, so that the catheter still has the required form after the sterilization process.

In the manufacture of catheters which bear a proximal hub or connecting member at one end, variations in length generally occur through unavoidable manufacturing variability. In order to be able to arrange catheters in the packaging according to the invention in a properly fixed manner, the part of the pressed-out portion which corresponds with and retains the hub or connecting member of the catheter comprises affixing means for affixing the hub or connecting member in a longitudinal position which may be varied. The affixing means thus ensures that the hub or connecting member can be arranged immovably in the packaging irrespective of variations from unit to unit of the longitudinal position of the proximal connecting member relative to the distal portion of the catheter.

Preferably, the affixing means accommodates the hub or connecting member in frictionally slidable relation so that the connecting member may be retained, while accommodating the inevitable differences in dimension of the catheter resulting from the manufacturing tolerances, particularly the length of the catheter between the curved distal tip and the proximal connecting member.

Additionally, the affixing means may comprise an added, separate, sheet-like member for connection to at least one of the sheets of the packaging. The sheet-like member defines a recess receiving the proximal connecting member of the catheter in affixed relation. Such a recess can receive the connecting member in a precisely fitting manner so that it does not become wedged in the packaging. The removal of the catheter from the packaging is thus facilitated.

The packaging is usually opened by pulling the two sheets away from one another at the end close to the connecting member. In the case of the embodiment with a separate, sheet-like member for affixing the connecting member, the latter is released directly on opening of the packaging by pulling the two sheets away from one another, so that the catheter can be withdrawn from the packaging easily by grasping it at the connecting member.

Further in accordance with this invention, in order t accomplish the second object of this invention described above, at least one of the elongated, flexible sheets of the packaging of this invention define or carry an inner layer of polyethylene, the sheet which carries such polyethylene layer being made of a material other than polyethylene. Preferably, both of the elongated, flexible sheets define an inner polyethylene layer and are made of a material other than polyethylene. One or both of the polyethylene layers face inwardly on the sheet for sealing fixedly to the other sheet.

Surprisingly and unexpectedly, it has been found that the damage to the catheters packaged in prior art blister packages results from the distal tip of the catheter rubbing or brushing along the inside of the packaging during withdrawal of the catheter immediately prior to use. Equally surprisingly, it has been found that such damage occurs during rubbing contact with a large variety of plastics typically used in the manufacture of blister packages, but not with polyethylene. Thus, since it is generally undesired to use polyethylene as a sheet material in such blister packages, it has been found that by using a blister package sheet of a desired material that carries on its inside a layer of polyethylene, the damage to the catheter may be prevented, while the high quality of the catheter and the packaging in accordance with this invention remains preserved.

The invention is particularly desirable for use where the peripheral sealing connection of the two sheets of the blister packaging lies in spaced relation from one end of the packaging, in order to form an end region in which the packaging sheets are free one of another. This permits manual opening by tearing of the blister packaging in a conventional manner.

The catheter is subsequently pulled out of the packaging in lengthwise direction, as is conventional. This creates the potential for damage of the catheter. However, by this invention, the inner polyethylene layer can wholly prevent such damage.

One of the sheets of the packaging in accordance with this invention typically comprises a paper which is permeable to sterilizing gas. Nevertheless, the inner layer of this paper may be provided with an inner polyethylene layer in preferred embodiments of this invention.

A great variety of materials may be used to provide the elongated, flexible sheets for blister packaging while carrying an inner layer of polyethylene. The polyethylene is therein used to achieve catheter protection and also improve peripheral sealing of the sheets together. One embodiment of a blister package for an angiographic catheter as described herein may use a flexible sheet of PET-G, which is a glycol-modified polyethylene terephthalate. The heat sealability of this material is very good for the manufacture of blister packaging. Such a sheet may be bonded to an opposed, paper sheet.

DESCRIPTION OF THE DRAWINGS

The invention will be further elucidated in the following description with reference to the embodiments shown in the figures.

FIG. 1 shows a packaging according to the invention in partly broken away, perspective view;

FIG. 2 shows a portion of the packaging from FIG. 1 on a larger scale;

FIGS. 3 and 4 show parts of the packaging from FIGS. 1 and 2 in curved position;

FIG. 9 shows another embodiment of packaging according to this invention in partly broken away perspective view;

FIG. 10 shows a proximal portion of the packaging of FIG. 9 on an enlarged scale; and FIG. 11 shows a section of the packaging along line 11-11 of FIG. 1.

DESCRIPTION OF SPECIFIC EMBODIMENTS

Figure 5:
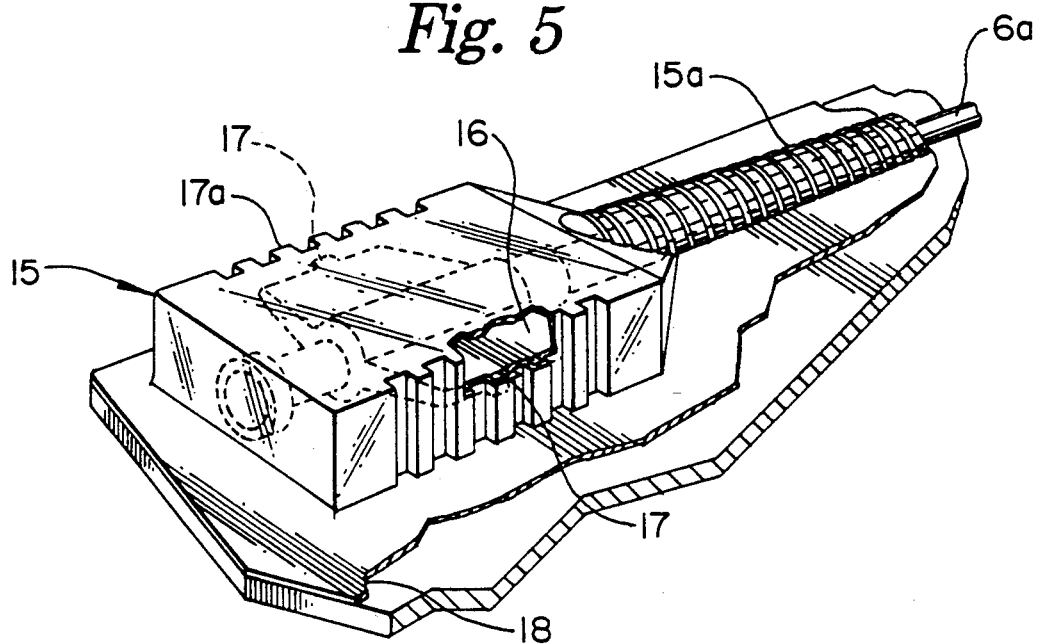
FIG. 5 shows an alternative embodiment of the proximal portion of a packaging according to the invention.

The packaging 1 shown in FIGS. 1-4 is intended for an angiographic catheter 6 which is thin and elongated. The packaging 1 is embodied as a so-called blister pack and comprises a lower sheet 2 and an upper sheet 3 which is laid on the first sheet 2 and connected thereto along the edges 4 by a heat treatment. The upper sheet 3 consists preferably of a transparent plastic while the lower sheet 2 is typically made of plastic or plastic-coated paper or cardboard.

A pressed-out portion 5 is formed in the upper sheet 3 so that a space is formed between the sheets 2 and 3 at the location of the pressed-out portion, in which space the catheter 6 is received. As FIG. 2 clearly shows, the pressed-out portion 5 has a corrugated profile. Thus, there is defined in the lengthwise direction of the pressed-out portion 5, arcuate wave tops 7 and wave hollows 8. As a result of this corrugated profiling of the pressed-out portion 5, the sheet 3 can bend in a flexible manner without such great stresses occurring in the pressed-out portion 5 that the material of the sheet 3 collapses or tears.

FIG. 3 shows a portion of the packaging with the pressed-out portion 5 which is curved spherically while FIG. 4 shows a corresponding portion which has hollow curves. In the situation in FIG. 3 the waved or corrugated profile in the upper portion of the pressed-out portion 5 is slightly stretched, while in the situation of FIG. 4 it is pressed slightly inwardly. With this deformation only relatively small bending loads occur in the material. If the pressed-out portion 5 was formed in the manner usual for blister packs, that is to say with a smooth, continuous wall without the corrugated profile, a high concentration of tension occurs very rapidly when bending takes place such that the material buckles and tears. Leaving aside the objection of the shabby appearance of a packaging with such buckles, the catheter carried in such a packaging can also become unusable because the sterility may no longer be ensured, and the catheter may also be damaged.

The pressed-out portion 5 of the packaging shown in FIG. 1 has a curved distal end portion 10 which is intended for receiving the distal end of the catheter for packaging. The package end portion 10 is curved in a corresponding form to the desired shape of the distal catheter end it contains. Specifically, the end part 10 of the pressed-out portion is dimensioned and geared to the catheter for packaging such that, in the packaged state, the curved distal end of the catheter is locked against bending out of its particular desired form.

Thus, during a sterilizing treatment carried out after the catheter has been packaged, the assembly of packaging and catheter can be subjected to an increased temperature. Normally, the danger arises that the curved form of the distal catheter end formed by thermoplastic processing may to a greater or lesser extent be distorted. However, because the curved outer end of the catheter remains enclosed in the pressed-out portion and thus retained in its desired shape, the catheter shape is preserved despite exposure to high temperatures.

In the manufacture of long catheters, variations in the total length of the catheter inevitably occur through inherent variations within manufacturing tolerances. Thus the position of the coupling or connecting member at the catheter proximal end may vary some millimeters relative to the curved distal end portion of the catheter.

FIG. 5 shows a portion of a packaging according to the invention which can still affix the coupling member well despite such variations. As shown, the upper sheet 18 in this embodiment comprises a pressed-out portion 15 which is enlarged at the position where the coupling member 16 of a catheter 6a resides. This pressed-out portion 15 also has a corrugated profile along most of its length. The catheter coupling member 16 of the catheter may be provided on either side with projections 17 which can fall into oppositely situated wave tops 17a of the pressed-out portion 15. The pressed-out portion 15 has a greater length than the coupling member 16, so that the coupling member can be arranged in the pressed-out portion 15 in a range of different positions, corresponding with the location of the wave tops 17a. Through the engaging of the projections 17 in the profile of the pressed-out portion 15, the coupling member 16 and therefore the catheter is properly locked in lengthwise position.

Figure 6:
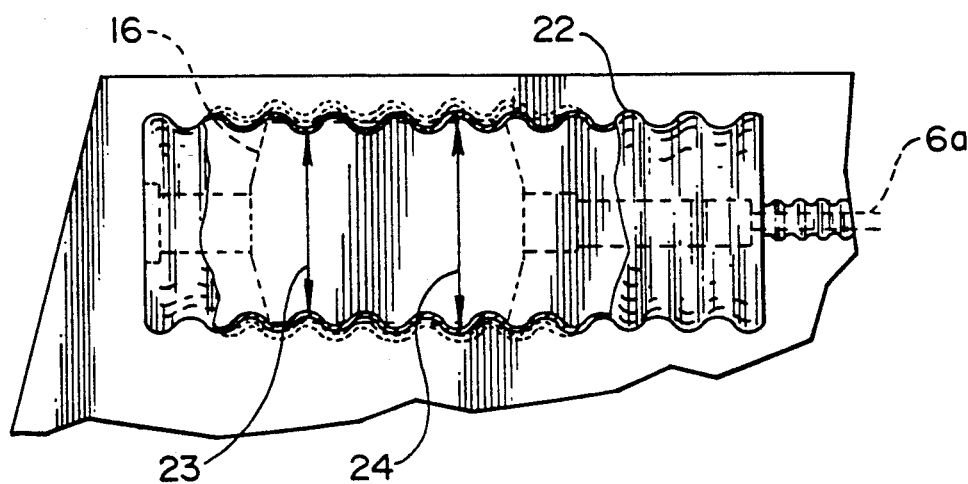
FIG. 6 shows a partly sectional top view of a proximal portion of an alternative embodiment.

In the embodiment of FIG. 6 the pressed-out portion 22 likewise has a corrugated profile. The transverse distance between wave hollows facing each other, which distance is indicated with arrow 23, is made somewhat smaller than the width of the coupling member 16, designated with dashed lines, while the distance between the wave tops as indicated with arrow 24 is greater than this width dimension of the coupling member 16. When the catheter is laid into the pressed-out portion of the packaging, the coupling member 16 is pressed into the pressed-out portion 22, to thereby deflect into the position indicated with broken lines. Through the waved shape of the pressed-out portion, this deflection takes place without damage to the material. The coupling member can therefore be held in a variable lengthwise position in the pressed-out portion 22 through friction provided by the inwardly-pressing wave hollows.

Figure 7:
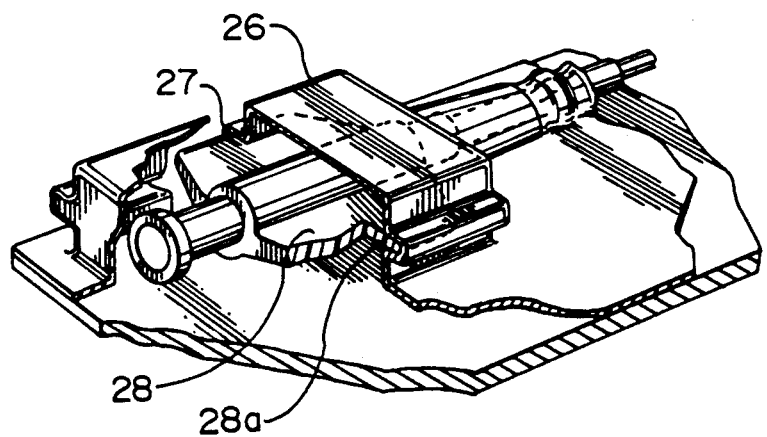
FIG. 7 shows a view corresponding with FIG. 5 of a portion of an alternative embodiment.

With the alternative embodiment in FIG. 7 the pressed-out portion 26 is provided with recesses 27 which can receive the edges of the wings 28a of the coupling member 28 at the proximal end of the catheter. The recesses 27 are dimensioned such that they can slidably accommodate the coupling member 28 with friction.

Figure 8:
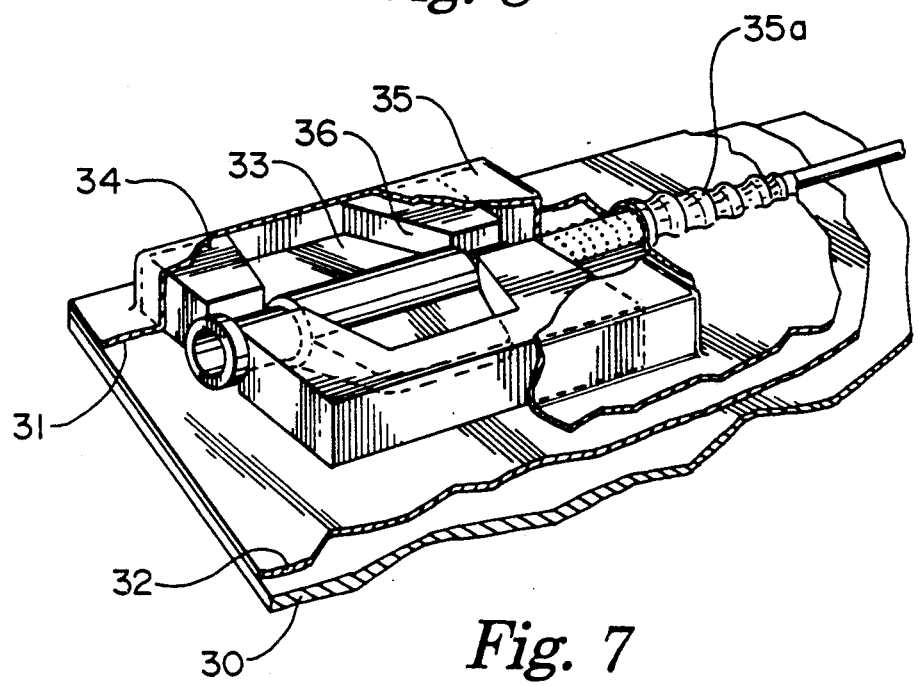
FIG. 8 shows a corresponding view of yet another embodiment.

With the packaging in FIG. 8 the catheter coupling member 33 is arranged in a variable longitudinal position in the packaging without friction, but in a close-fitting manner. Arranged between the lower sheet 30 and the upper sheet 31 is a sheet-like member 32 which is provided with a bulge 34 which defines a cavity 36 wherein the coupling member 33 is close-fittingly arranged. A corresponding pressed-out portion 35 in the upper sheet 31 is formed such that the bulge 34 of the sheet-like member 32 can be arranged therein in a variable longitudinal position to accommodate for variations in catheter length.

During packaging of the catheter, the coupling member 33 is laid in the cavity 36 of the loose sheet 32. The remaining part of the catheter is laid in the pressed-out portion 35a of the upper sheet 31, whereby the bulge 34 of sheet 32 occupies a longitudinal position in the pressed-out portion 35 as determined by the specific length of the catheter. When the thus-assembled packaging is then sealed, the lower sheet 30 and upper sheet 31 are sealed together along their edges in the previously described manner, and the holder sheet 32 is also sealed into position with sheets 30 and 31. The sheet 32 is thus fixed relative to the upper sheet 31 and the lower sheet 30, and in this way the coupling member 33 is fixed in the lengthwise direction of the catheter.

The packaging is further embodied such that when the packaging is opened by pulling the sheets away from each other, the sheet-like member 32 is taken away with the lower sheet, so that the upper sheet 31 is therefore pulled loose from the sheet-like member 32, and the coupling member 33 can be released from the cavity 36 in an upward direction. It is of course also possible to provide a sheet-like member where its cavity for the coupling member is accessible from below, and that when the packaging is pulled open, the sheet-like member with the cavity is taken along by the upper sheet.

The sheet of the packaging provided with the pressed-out portion can be formed in a per se known manner for blister packs by subjecting a thermoplastic plastic material to a vacuum forming technique.

When a hermetic packaging is not necessary, as it is with catheters, the sheet of the packaging carrying the pressed-out portion can for example be of a suitable, thin cardboard, and the pressed-out portion with the corrugated profile can be arranged therein by a pressing operation. The invention is not limited to the manufacture of the packaging with a specific design technique. All techniques which can arrange an elongated, pressed-out portion having at least partly a corrugated profile in a flexible sheet are applicable for the invention.

In addition to the use for packaging elements which are themselves thin and elongate, such as catheters, the packaging according to the invention can also very well be used for elements of which only a portion is thin and elongated. At the location of the thin, elongated portion, such packaging is preferably embodied with a pressed-out portion having a corrugated profile.

Referring to FIGS. 9 through 11, this embodiment of blister packaging 101, in a manner generally similar to the previous embodiments, comprises a first sheet 102 and a second sheet 103 which is laid on the first sheet 102 and connected thereto along the edges 104 by a peripheral heat seal, as is generally conventional. First sheet 103 comprises a preferably transparent plastic, while lower sheet 102 typically comprises paper, to permit the passage of ethylene oxide sterilization agent or the like.

Cavity 105 is pressed-out of the first sheet 103, which is typically made of a semi-stiff plastic material such as PET-G. Catheter 6b is positioned within cavity 105. As Fig. 10 particularly shows, the pressed-out portion 105 defines a corrugated profile, with convolutions in portion 105 defining arcuate wave tops 107 and wave hollows 108. As a result of this, the corrugated profiling of the pressed-out portion 105 permits sheet 103 of bend in a flexible manner without collapse or tearing of sheet 103.

The pressed-out portion 105 of the packaging 101 defines a curved distal end portion 100 which receives an outer end of the catheter 6b, which defines a distal tip forming a similar curve in its natural, unstressed configuration. The end part 100 of the pressed-out portion 105 is dimensioned so that the packed catheter 6b in the packaged state has its curved distal end locked against bending out of the particular corresponding form so that the distal end cannot bend out of its desired shape for reasons discussed previously.

The peripheral seal 104 between sheets 102, 103 on the left-hand side of the packaging 101 in FIG. 9 lies in spaced relation from the end of the sheets 102, 103, so that two lips 110, 120 of the respective sheets 102, 103 are formed in unjoined relation. In order to remove catheter 6b out of the packaging, lips 110 and 120 are gripped and pulled apart. The peripheral seal 104 adjacent to the package end carrying lips 110, 120 is thereby broken in the manner of a peel seal, and the connecting part or proximal hub of the catheter, positioned in widened part 150 of pressed-out portion 105, can be gripped. The catheter is then removed from the packaging by being pulled in lengthwise direction. The distal end part of the catheter slides through pressed out portion 105 between sheets 102 and 103, while rubbing along the mutually facing surfaces of these sheets.

To reduce or eliminate the problems of the prior art created by this situation, as shown in FIG. 11, sheet 103, which substantially comprises for example glycol-modified polyethylene terephthalate is preferably provided with a thin inner layer 170 of polyethylene on the side facing second sheet 102. Second sheet 102, which is typically made of paper can likewise be covered with an inner layer 190 of polyethylene. When the catheter 6b is pulled outwardly from the package, it therefore is in continuous contact with the polyethylene inner layers 170, 190, whereby the damaging wear and tear which occurs in prior art packages for catheters does not take place.

Since the paper of second sheet 102 is typically more flexible and yielding then the plastic of first sheet 103, the chance of damage through such wear and tear, as described above during the withdrawal of the catheter by rubbing along sheet 102, is considerably smaller. Thus, if desired, sheet 102 may not carry an inner layer of polyethylene in those circumstances where that is desirable.

The material of sheet 103 does not have to comprise only two layers. Instead of this, for instance, a continuous PET-G laminate can also be used having an inner polyethylene layer. Another material such as plastic may also be used instead of the paper for layer 102.

The above has been offered for illustrative purposes only, and is not intended to limit the scope of the invention of this application, which is as defined in the claims below.

That which is claimed is:

1. A catheter package, which comprises:
   an elongated, flexible catheter having a thin, fragile portion;
   a first elongated flexible sheet;
   a second elongated flexible sheet;
   means adhering said flexible sheets to each other and forming a space between said sheets receiving the catheter;
   said space being defined by a pressed-out portion generally corresponding to the shape of the catheter in said first sheet;
   said first sheet having a plurality of corrugations in the part of the pressed out portion corresponding with the thin, fragile, elongated portion of the catheter.

2. A catheter package, which comprises:
   an elongated, flexible catheter having a thin, fragile portion;
   a first elongated flexible sheet;
   a second elongated flexible sheet;
   means adhering said flexible sheets to each other and forming a space between said sheets receiving the catheter;
   said space being defined by a pressed out portion generally corresponding to the shape of the catheter in said first sheet;
   said first sheet having a plurality of corrugations in the part of the pressed out portion corresponding with a thin, fragile, elongated portion of the catheter;
   said catheter packaged therein having a distal end curved in a predetermined shape, in which the part of the pressed out portion corresponding with said curved distal catheter end is formed such that said curved distal catheter end is locked therein against being distorted out of shape;
   said catheter packaged therein having a connecting member at its proximal end, in which the part of a pressed out portion corresponding with said connecting member in one of variable longitudinal positions.

3. The package of claim 1 which carries a catheter packaged therein having a distal end curved in a predetermined shape, in which the part of the pressed-out portion corresponding with said curved distal catheter end is formed such that said curved distal catheter end is locked therein against being distorted out of said shape.

4. The package of claim 2, in which the affixing means frictionally retains the connecting member.

5. The package of claim 2, in which the affixing means comprises a separate, sheet-like member for connection to at least one of the sheets, and having a recess receiving the connecting member in affixed position.

6. The package of claim 2 which carries a catheter packaged therein having a connecting member at its proximal end, in which the part of the pressed-out portion corresponding with said connecting member comprises affixing means for affixing said connecting member in one of variable longitudinal positions.

7. The package of claim 6 in which the affixing means frictionally retains the connecting member.

8. The package of claim 6 in which the affixing means comprises a separate, sheet-like member for connection to at least one of the sheets, and having a recess receiving the connecting member in affixed position.

9. The package of claim 1 in which at least one of said elongated, flexible sheets defines an outer layer made of a plastic material other than polyethylene, and defines an inner layer of polyethylene in at least the area of said first sheet to be in contact with the element carried in the packaging.

10. The package of claim 9 in which the other of said elongated, flexible sheets comprises a paper sheet and carries an inner layer of polyethylene.

11. The package of claim 10 in which said elongated, flexible sheets are connected together with a peripheral seal, said peripheral seal being spaced from one end of said packaging, whereby an end region of the sheets are free and unconnected to facilitate manual opening.

12. In blister package for a catheter, which blister packaging defines a pair of elongated, flexible sheets peripherally adhered to each other with a seal, with the catheter retained within said peripheral seal in a central area where the flexible sheets are spaced from each other, the majority of the length of said catheter being positioned in a thin, elongated, outwardly projecting portion of said central area, the improvement comprising, in combination:

at least one of the elongate sheets defining said thin, elongated, outwardly projecting portion defining transverse corrugations, said one elongated flexible sheet which defines the transverse corrugations defining another layer made of a plastic material other than polyethylene, and defining a polyethylene layer on its inner surface, whereby said catheter contacts said polyethylene layer when being removed from the packaging.

13. The packaging of claim 12 in which the catheter packaged therein defines a connecting member at its proximal end, and in which the part of the central area enclosing said connecting member comprises means for affixing said connecting member in one of variable longitudinal positions.

14. The package of claim 13 in which the other of said flexible sheets comprises a paper sheet defining an inner polyethylene layer.

15. The packaging of claim 14 in which the affixing means frictionally retains the connecting member.

16. The packaging of claim 14 in which the affixing means comprises a separate, sheet-like member for connection to at least one of said sheets, said separate, sheet-like member defining a recess receiving said connecting member of the catheter in affixed position, said separate, sheet-like member being peripherally secured to said elongated, flexible sheets.

17. The package of claim 2 in which the affixing means frictionally retains the connecting member.

18. The packaging of claim 17 in which at least one of said elongated, flexible sheets defines an outer layer made of a plastic material other than polyethylene, and defines an inner layer of polyethylene in contact with said catheter.

19. The packaging of claim 18 in which the other of said elongated flexible sheets comprises a paper sheet and carries an inner layer of polyethylene in contact with said catheter.

* * * * *